, 
United States Patent [19]

Shields

[11] 4,011,595
[45] Mar. 15, 1977

[54] DEFOGGABLE GOGGLES

[76] Inventor: Michael Peter Shields, 6647 Glade St., Canoga Park, Calif. 91303

[22] Filed: Aug. 28, 1973

[21] Appl. No.: 392,253

[52] U.S. Cl. .............................................. 2/436
[51] Int. Cl.² ........................................ A61F 9/02
[58] Field of Search ............... 2/14 K, 14 D, 14 R, 2/14 B, 14 C, 14 N

[56] References Cited

UNITED STATES PATENTS

| 1,354,433 | 9/1920 | De-Felice | 2/14 K |
| 1,871,534 | 8/1932 | Kimball | 2/14 R |
| 2,430,881 | 11/1947 | Lehmberg | 2/14 D |
| 2,526,737 | 10/1950 | Farina | 2/14 K |
| 3,081,461 | 3/1963 | Gurtowski | 2/14 D |

Primary Examiner—Werner H. Schroeder
Assistant Examiner—Peter Nerbun
Attorney, Agent, or Firm—Lyon & Lyon

[57] ABSTRACT

Goggles having a wide lens mounted in a semi-rigid frame which positions the lens away from the face providing an enclosed air space, the frame having a number of apertures permitting an influx of air, and one or more outlet apertures to which are secured means for evacuating air from the inner space. The evacuating means takes the form of a conduit which can be placed in the wearer's mouth to draw air out of the inner space.

8 Claims, 10 Drawing Figures

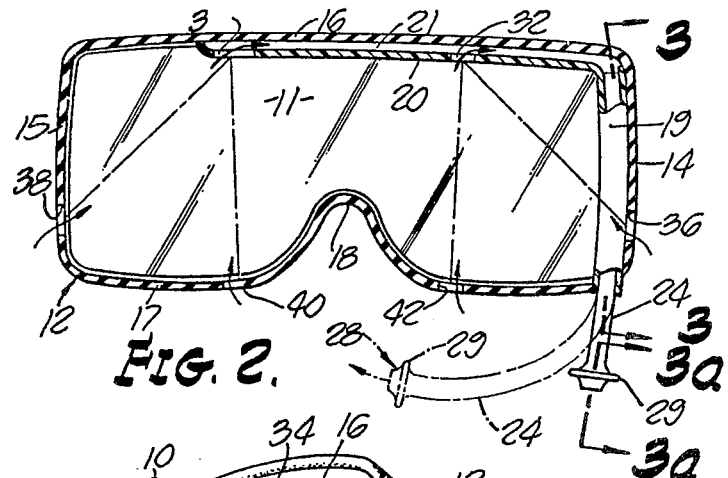
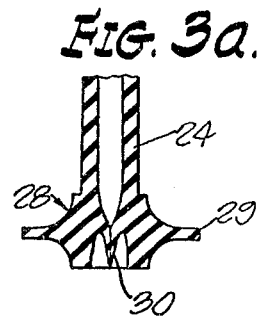
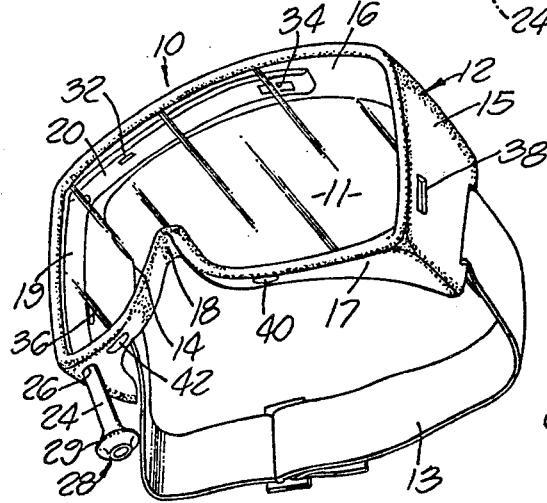
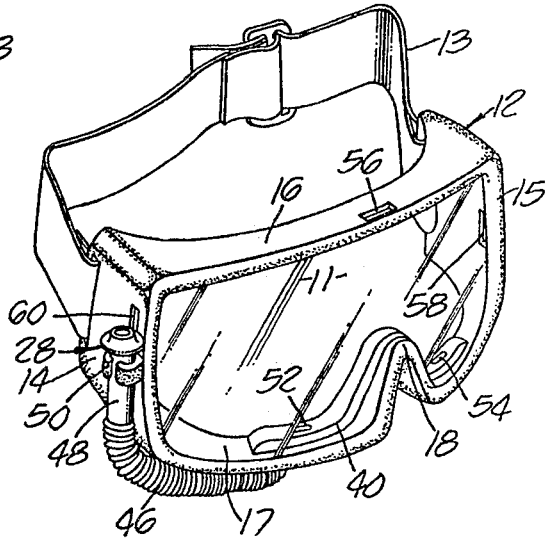
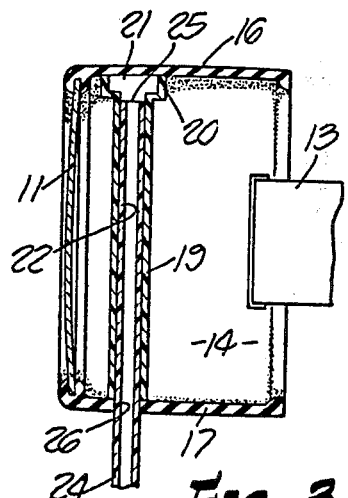
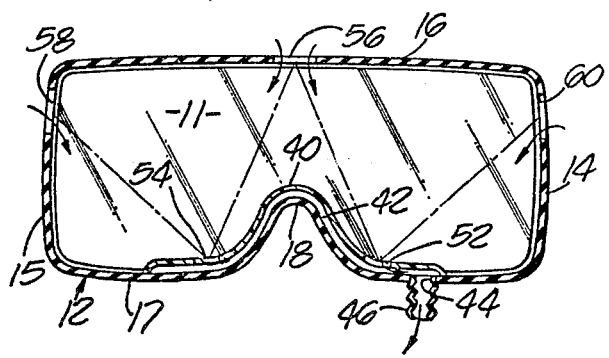

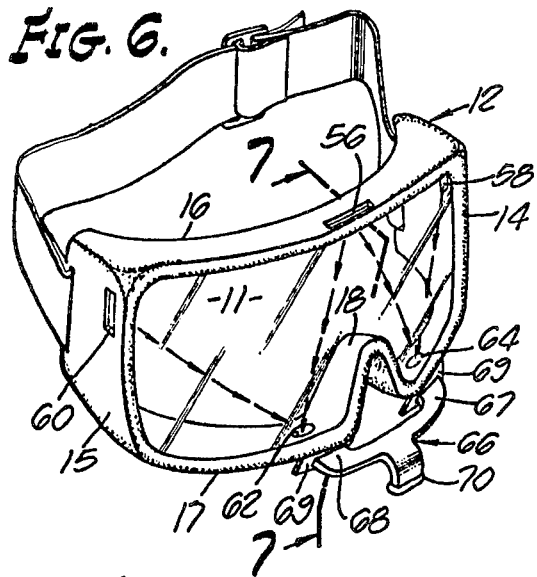
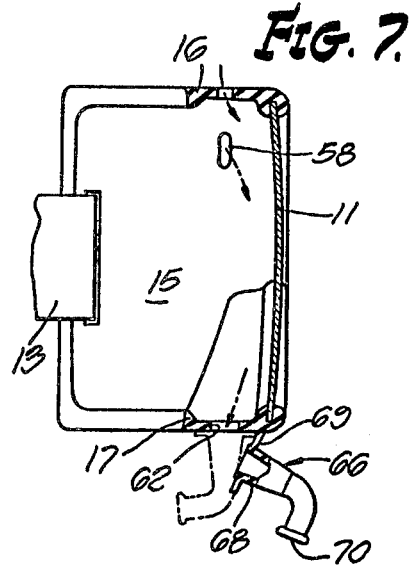
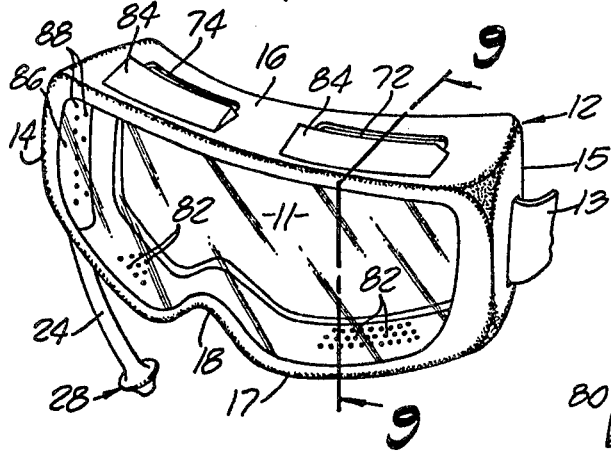
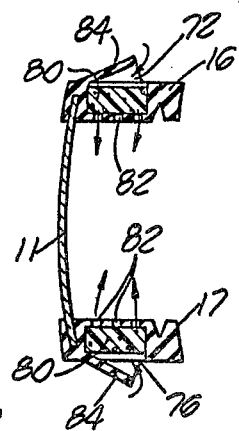

DEFOGGABLE GOGGLES

BACKGROUND OF THE INVENTION

This invention relates generally to goggles, and more particularly to goggles useful for athletics and similar activities performed in cold weather, other outdoor activities such as motorcycling and the like. Heretofore, goggles employed for the above-mentioned purposes have been subject to the accumulation of condensation or fog upon the interior surfaces of the lens. In order to be effective for many activities, a goggle must fit tightly to the contour of the wearer's face so as to keep snow, water and/or dust out of the user's eyes, but tight fitting goggles which confine an air space around the eyes of the user will fog in a short time, particularly when worn when the ambient temperature is low or when the exterior surface of the lens is cooled by the wind. Such fogging occurs because of an increase of humidity inside the inner space as the result of perspiration of the user, and is a particular problem with increased bodily activity. With increased activity of the wearer, the humidity can rise sufficiently to completely and rapidly cloud the vision of the wearer, particularly after the wearer has come to rest following strenuous activity.

A great many goggles have been heretofore designed in an effort to alleviate this problem, however all of the known solutions bear certain shortcomings. One of the solutions to this problem has been to ventilate the frame portion of the goggles by providing a large plurality of apertures so as to permit a circulation of air through the inner space. The provision of a large number of apertures as may be necessary to afford sufficient means for air circulation decreases the effectiveness of the device to prevent the entrance of snow or dust. In addition, apertures which permit the entrance of snow, moisture or dust inside the goggle will also allow the same to accumulate on the inside of the lens where it will adhere, further decreasing visibility. Furthermore, ventilating holes permit the penetration of cold air causing discomfort to the face, eyes and nose of the wearer under cold temperature conditions. Such ventilating apertures also suffer from the difficulty that they are only effective when the wearer is moving so that air is forced through the goggles and these apertures cease to operate effectively when the wearer comes to rest.

Another solution to the aforementioned problems has been a double lens arrangement having sealed air space between two lenses so that the inner lens is not excessively cooled and therefore the likelihood of condensation occuring thereon is decreased. It has been observed, however, that such double lens goggles are not entirely effective without the provision for some means for ventilating the inner space as previously described, with the inherent shortcomings already mentioned. A further disadvantage of the double lens construction is the increased cost of manufacture. Another problem arises in that users of goggles frequently wear them over their ordinary eyeglasses and it has been found that whether or not the inside of the lens fogs, one or both sides of the eyeglasses will fog. None of the known constructions provides a mechanism which will prevent or eliminate the fogging of the eyeglasses. While there exists a considerable body or prior art disclosing the concept of providing forced air circulation for goggles and face masks, such systems do not readily lend themselves to the use of goggles for sports activities and the like inasmuch as they require air pressure devices for circulating the air. In addition, such positive pressure devices raise the inside air pressure which tends somewhat to decrease the ability to remove condensation from the inner surfaces.

SUMMARY OF THE INVENTION

It is a principal object of the present invention to provide sports goggles of simple and economical construction having means for quickly and readily evacuating air from the inner space to thereby rapidly remove condensation from the interior surfaces thereof as well as any condensation which may collect upon the eyeglasses of the wearer. It is therefore the primary object of this invention to provide an improved goggle which can, in use, be readily cleared of condensation, yet which is simple in construction, comfortable to wear and otherwise poses the least restrictions to visibility.

The foregoing objects are accomplished in the present invention by providing goggles having but a few small inlet apertures at spaced locations about the walls of the frame which permit an influx of air, together with means attached to one or more further apertures provided in the frame to which are affixed menas by which the air within the inner space may be rapidly and effectively evacuated. By pulling air out of the inner space, a slight vacuum is created therein as a result of the fact that the inlet apertures are small so that air is only gradually allowed to reenter the air space, with the result that the vapor pressure of the condensate contributes to a more rapid evaporation thereof. This taken together with the effect of the circulation of air within the inner space as it comes through the inlet apertures, removes the condensate from the inner surface of the lens or lenses more rapidly and effectively than the other known structures.

In several of the embodiments of the present invention set forth herein, the evacuating means comprises a conduit which can be collapsibly affixed to the frame and which can be extended and placed in the mouth of the wearer so that he can by sucking upon it draw air out of the inner space.

Further objects and advantages of the present invention will become readily apparent to those skilled in the art upon reading the ensuing detailed descriptions of the various embodiments in conjunction with the accompanying drawings.

DESCRIPTION OF THE DRAWINGS

FIG. 1 is a perspective view of a first embodiment of the present invention.

FIG. 2 is a sectional rear view of the first embodiment shown in FIG. 1.

FIG. 3 is a sectional and elevation taken along line 3—3 of FIG. 2.

FIG. 3a is a sectional detailed view of the mouthpiece taken along line 3a—3a of FIG. 2.

FIG. 4 is a perspective view of a second embodiment of the present invention.

FIG. 5 is sectional rear view of the embodiment shown in FIG. 4.

FIG. 6 is a perspective view of a third embodiment of the present invention.

FIG. 7 is a partial sectional end view of the third embodiment taken along line 7—7 of FIG. 6.

FIG. 8 is a perspective view of a fourth embodiment of the present invention.

FIG. 9 is a sectional and elevation of the fourth embodiment taken along line 9—9 of FIG. 8.

DESCRIPTION OF THE FIRST EMBODIMENT

The goggles generally designated 10 comprise a lens 11 supported in spaced relation to the wearer's face by a frame structure 12 and are held in position by an elastic band 13 which engages the frame 12 and encircles the wearer's head. The lens 11 is secured within the frame 12 by any conventional means and may be either permanently affixed therein or can be mounted so that the lens is interchangeable by various means well known in the art. All of this design is conventional. The frame 12 is made of a resilient, flexible material, normally a soft plastic or rubber and the rear edge of the frame is arcuate so as to conform to the face of the wearer in the area of his eyes. The rear edge of the frame may be provided with a foamed plastic or rubber or otherwise soft or resilient material cemented to the frame material so as to more readily conform the frame to the wearer's face, to cushion the frame against his face and forehead and to seal the edges of the frame to his face thereby creating a closed inner air space between the face of the user and the interior of the frame and lens construction. The foam or plastic material on the rear edge of the frame is not shown in the drawings, the use of such material on goggles and the like being quite conventional however such point is mentioned herein in that it is desirable in the present invention that there be a tight seal between the frame and the wearer's face for purposes which will be more readily apparent hereafter and while it is possible to obtain such a seal using conventional resilient material for the construction of the frame itself, it is preferable to use the additional sealing material. Any such sealing material utilized for this purpose should preferably be of the type which is non-porous so that air flow through the sealing material is substantially restricted.

The frame 12 consists of side pieces 14 and 15 an upper wall 16 and a lower wall 18 formed as an integral unit. The lower unit 17 is, of course, provided with a nose bridge portion 18. A tubular housing 19 is secured to the inner surface of either of the sidewalls 14 or 15, FIG. 1 showing this housing adhering to sidewall 14 although it would be obvious to mount this housing on either side. A manifold 20 is formed along the inner surface of the upper wall 16. This manifold 20 extends longitudinally across the inner surface of wall 17 from the sidewall 14 but extends less than the total distance across to the other sidewall 15. This manifold 20 provides a passage 21 the interior of which is in communication with the interior passage 22 of the tubular housing 19. A flexible tube member 24 is slidably mounted within the tubular housing 19 and extends through an aperture 26 formed in the bottom wall 17 of frame 12. The tube 24 is provided having an outside diameter substantially equal to the inside diameter of tubular housing 19 so that a close fitting relationship is maintained therebetween. The inside end 25 of tube 24 is free and unattached. The other end is provided with a mouthpiece construction 28 having an enlarged annular portion 29 and a one-way valve element 30 (see FIG. 3a). The tube member 24 and the mouthpiece 28 can all be constructed as an integral unit made of soft plastic or rubber material and the valve element 30 formed integrally therein. The longitudinal manifold 20 is provided with a number of apertures therein which communicate the interior passage 21 with the inner space of the goggles behind the lens. The first aperture 32 which is located nearest the housing 19, but spaced therefrom, is of smaller size than the second aperture 34 which is located near the end of manifold 20 and spaced a greater distance from the housing 19. Actually, aperture 32 is positioned in the right half of the goggle housing generally above the right half of the eye piece and aperture 34 is similarly positioned over the left half of the eye piece.

A plurality of inlet apertures are provided in the sidewalls and bottom wall of the frame. Aperture 36 is formed in sidewall 14 and aperture 38 in sidewall 16 while apertures 40 and 42 are formed in the bottom wall 17 on each side of the bridge section 18. The locations of the inlet apertures 36, 38, 40 and 42 are chosen with respect to the outlet apertures as shown by the phantom lines in FIG. 2.

When the goggle is used in the proper manner, tightly secured to the wearer's face, the wearer upon experiencing condensation on the lens, extends the conduit tube 24 which is flexible and places the mouthpiece 28 in his mouth. By drawing inwardly thereon, a slight vacuum is created in the inner space and air will be pulled into the inner space through the apertures 36, 38, 40 and 42. By placing the inlet apertures at locations which are equadistant from the outlet apertures 32 and 34, the decrease in pressure within the goggle will be substantially uniformly distributed throughout the volume of the inner space and by properly choosing the sizes of those inlet apertures, this slight vacuum can be maintained for a short period of the time. In addition to controlling this slight vacuum by means of the size and location of the inlet apertures, the location of said inlet apertures also sets up a pattern of air flow from the inlets to the outlets which is substantially uniform within the inner space thereby further enhancing the evaporative capabilities thereof. By stationing the inlet apertures and the outlet apertures in positions close to the rear surface of the lens 11, most of the air flow will pass closely over the rear surface of the lens thereby more rapidly removing the condensation therefrom. The provision of the valve element 30 in the mouthpiece 28 permits the wearer to retain the mouthpiece in his mouth for prolonged periods of use whereby he can draw air out of the goggle at any time he experiences fogging yet the valve will prevent any breath which he exhales from entering the goggle. Further advantages of the valve element 30 will become apparent upon the ensuing discussion of some of the further embodiments of the invention.

DESCRIPTION OF THE SECOND EMBODIMENT

Referring now to FIGS. 4 and 5, a second embodiment of the invention is shown employing many of the same features disclosed in the first embodiment except in respect to the type and location of the air evacuation means. In the second embodiment, like reference numerals refer to like structural features. In this embodiment the outlet manifold 40 is located upon the lower wall 17 and extends over the bridge portion 18. As before, this manifold comprises a hollow member having an interior passage 42. An aperture 44 is formed in the lower wall 17 communicating with passage 42 and to aperture 44 is connected a flexible conduit member 46 to the other end of which may be connected a short section of non-flexible conduit 48 to which is connected the mouthpiece 28. A split ring 50 may be affixed to the sidewall 14 of the frame to removably receive the flexible conduit 46, 48. Manifold 40 is provided with two outlet apertures 52 and 54 stationed on each side of the bridge section 18. Inlet apertures are formed in the frame; one inlet aperture 56 being positioned in the upper wall 16 above the bridge secton 18 and apertures 58 and 60 are formed in sidewalls 15 and 14 respectively. Here again, the positions of the inlet and outlet apertures are selected so as to provide equadistant paths for the flow of air from the inlets to the outlets for the purposes previously described.

DESCRIPTION OF THE THIRD EMBODIMENT

Referring now to FIGS. 6 and 7, this embodiment is similar in construction to the embodiments shown in FIGS. 4 and 5 in that the location of the inlet apertures 56, 58 and 60 are the same but in place of the internally situated outlet manifold 40, the lower wall 17 is provided with outlet apertures 62 and 64 located on each side of the bridge portion 18 of the frame. An external manifold 66 having lateral arm portions 67 and 68 is hingedly mounted to the lower wall 17 by flanges 69 affixed to the lateral arms 67 and 68. The ends of the arms 67 and 68 project slightly through the flanges 69 as can be seen in FIG. 7. Manifold 66 is further provided with a mouthpiece section 70.

The use of this embodiment can best be understood from viewing FIG. 7. The manifold section 66 can be pivoted counterclockwise, as shown in FIG. 7, so that the lower apertures 62 and 64 are open, thereby permitting free circulation within the inner space. When fogging is experienced, the pivotal manifold 66 is moved clockwise ( in FIG. 7) so that the user may place the mouthpiece section 70 in his mouth. In this position, the flanges 69 surround the apertures 62 and 64 and the ends of the arms project slightly into the outlet apertures 62 and 64. Thus, the outlet apertures are closed by the arm elements of the manifold and the user may then evacuate air from the interior of the frame as previously described. Again, the location of the inlet and outlet apertures are chosen so as to provide equadistant airpaths for the purposes and advantages already mentioned. As in the previous embodiments, mouthpiece 70 may be provided with one-way valve means if desired.

DESCRIPTION OF THE FOURTH EMBODIMENT

Referring to FIGS. 8 and 9, several additional features of the present invention are shown, and these features may be selectively employed in conjunction with the various embodiments previously described. In this modification of the invention, the inlet apertures 72 and 74 comprise enlarged recessed portions formed in the top wall 16 of the frame 12. Similarly, inlet apertures may also be formed in the same manner in the lower wall 17. FIG. 9 is a cross-sectional view showing the inlet aperture 72 formed in the top wall 16 and another inlet aperture 76 formed in the lower wall 17. These apertures 72 and 76 as well as the other inlet apertures formed in the top and bottom walls are enlarged recesses of generally rectangular configuration in which are removably inserted pieces of filter material 80 which substantially fill these recessed openings and cover a plurality of small apertures 82 formed in the bottom of these recessed portions. These small apertures are several in number as can be seen in FIG. 8 and are distributed in the top and bottom walls over a considerably greater area than that of the inlet apertures previously described. The number and location of these apertures will differ depending upon the location of the outlet apertures so that the change in pressure can be equalized within the inner space and the flow of inlet air under the influence of the slight vacuum created therein can be equalized. In addition, the inlet apertures are partially covered by hood portions 84 which slant upwardly from the front portion of the goggle frame as shown in FIG. 9. In this manner, these rather large inlet apertures are substantially protected from incoming moisture, snow or dirt when the wearer of the goggles is moving.

In place of the transversely disposed outlet manifold 20 of the first embodiment, the present embodiment utilized the vertically located tubular housing 86 as an outlet manifold by providing the same with a plurality of apertures 88 formed along the length thereof. The number of such apertures which will be effective in use will depend upon the extent to which the outlet conduit 24 is withdrawn from the tube portion 86. FIG. 8 shows that the number of inlet apertures 82 located near the outlet apertures 88 is fewer in number than those located more distant therefrom. As previously described this accomplishes an equalization of the pressure differential within the inner space when the air is being evacuated therefrom.

The use of the filter material 80 over the inlet apertures provides an additional advantage for the present invention. The goggles may be used in high dust or heavy snow conditions without harm or discomfort to the user in that the user may place the mouthpiece 28 in his mouth for continuous use providing him with a means for inhaling filtered air continuously. The advantage is that he can inhale filtered air while at the same time preventing condensation from forming on the inside of the lens or upon any eyeglasses he might be wearing.

While I have shown herein several embodiments of my invention, it will be apparent that throughout these embodiments there runs a common concept in that I have employed the use of a slight vacuum applied to the interior of the goggle frame when the goggle is properly worn and I have found that the application of a slight vacuum within this inner space creates a condition which clears the interior of the goggle from accumulated condensation more rapidly than previously known devices of this type. It is believed that this is the result not only of an increase in air circulation as the result of the vacuum created, but also that the slight vacuum itself which exists for a period of time within the inner space takes advantage of the inherent vapor pressure of the condensate such that its rate of evaporation is further enhances particularly over those prior art devices which increase the air pressure within articles of this type. In addition to the foregoing advantages, the present invention provides goggles which can be continuously cleared of condensation without appreciably interferring with the user's respiration, even when the user's respiration rate is higher than normal due to strenuous physical activity. It is not the intention hereof to limit the details of my invention to the precise embodiments shown herein as it is intended that this invention be defined by the lawful scope of the appended claims.

I claim:

1. Improved goggles of the type having a lens mounted in a one piece frame structure which includes rearwardly extending side, top and bottom peripheral wall members the rear edges of which are shaped to conform closely to the face of the wearer extending about the eyes and over the nose thereby defining an enclosed inner airspace between the lens and the face of the wearer, the improvement comprising:

two or more air inlet apertures formed in a first one or more of said wall members, manifold means affixed to one of said wall members other than said first wall members, said manifold means having an internal passage, means connecting said passage with said enclosed airspace, a housing having a chamber, said housing being coupled to and forming a part of said manifold, said chamber communicating with said passage; and conduit means coupled to said manifold means, said conduit means extending externally of said frame structure a distance sufficient to reach the mouth of the wearer thereof when said frame structure is positioned about the eyes and over the nose of the wearer, said chamber adapted to slideably receive said conduit means therein.

2. Improved goggles of the type having a lens mounted in a one-piece frame structure which includes rearwardly extending side, top and bottom peripheral wall members, the rear edges of which are shaped to conform closely to the face of the wearer extending about the eyes and over the nose thereby defining an enclosed inner air space between the lens and the face of the wearer, the improvement comprising:

two or more air inlet apertures formed in a first one or more of said wall members, manifold means affixed to an internal surface of one of said wall members other than said first wall members, said manifold means having an internal air-conducting passage, a plurality of outlet apertures formed in said manifold means communicating said internal passage with said enclosed air space, conduit means coupled to said manifold means and communicating with said internal passage, said conduit means extending externally of said frame structure and having a length sufficient to reach the mouth of the wearer when said frame structure is positioned about the eyes of said wearer;

said conduit means being connected to said manifold means near one end of the internal air-conducting passage thereof, one of said outlet apertures being located nearer the point of connection of said conduit means to said manifold means than said other outlet apertures, the size of said apertures nearer said point of connection being smaller than that of said apertures more distantly placed.

3. The article set forth in claim 2 further including a housing defining a chamber, said housing coupled to said manifold means whereby the chamber thereof communicates with said internal passage, said chamber slideably receiving said conduit means therein, said conduit means comprising a flexible tubular member.

4. The article set forth in claim 2 wherein said inlet and outlet apertures are positioned symmetrically about said peripheral frame structure, said outlet apertures being spaced uniform distances from said inlet apertures.

5. The article set forth in claim 2 wherein said internal passage of said manifold means slideably receives said conduit means therein.

6. Improved goggles of the type having a lens mounted in a one-piece frame structure which includes rearwardly extending side, top and bottom peripheral wall members, the rear edges of which are shaped to conform closely to the face of the wearer extending about the eyes and over the nose thereby defining an enclosed inner air space between the lens and the face of the wearer, the improvement comprising:

two or more air inlet apertures formed in a first one or more of said wall members, manifold means affixed to an internal surface of one of said wall members other than said first wall members, said manifold means having an internal air-conducting passage, a plurality of outlet apertures formed in said manifold means communicating said internal passage with said enclosed air space, conduit means coupled to said manifold means and communicating with said internal passage, said conduit means extending externally of said frame structure and having a length sufficient to reach the mouth of the wearer when said frame structure is positioned about the eyes of said wearer;

said manifold means extending across the internal surface of the top wall member, said inlet apertures being located in said side and bottom wall members, said manifold means being connected at one end thereof to a housing situated along one of said side wall members, said housing having a chamber which communicates with the internal passage of said manifold, said housing slidably receiving said conduit means therein; said outlet apertures formed in said manifold means being positioned symmetrically with respect to said inlet apertures.

7. The article set forth in claim 6 wherein the outlet aperture in said manifold which is located nearest to the said housing is smaller than apertures spaced more distant therefrom.

8. Improved goggles of the type having a lens mounted in a one piece frame structure which includes rearwardly extending side, top and bottom peripheral wall members the rear edges of which are shaped to conform closely to the face of the wearer extending about the eyes and over the nose thereby defining an enclosed inner airspace between the lens and the face of the wearer, the improvement comprising:

two or more air inlet apertures formed in said top and side wall members, said bottom wall member having a nose-bridge section, outlet apertures formed in said bottom wall member on each side of said nose-bridge section, manifold means hingedly mounted upon the external surface of said bottom wall member, said manifold means having arm members adapted to register with said outlet apertures when said manifold is moved to a first position, said manifold arm members disengaging from said outlet aperture when said manifold is in a second position, said manifold having a conduit coupled to said arm members, said conduit when in said first position having a length and configuration sufficient to reach the mouth of the wearer when said frame structure is positioned about the eyes of the wearer.

* * * * *